(12) United States Patent
De The et al.

(10) Patent No.: US 8,784,797 B2
(45) Date of Patent: Jul. 22, 2014

(54) METHODS, PHARMACEUTICAL COMPOSITIONS AND KITS FOR USE IN THE TREATMENT OF ADULT T-CELL LEUKEMIA/LYMPHOMA

(75) Inventors: Hugues De The, Paris (FR); Ali Bazarbachi, Beirut (LB); Olivier Hermine, Paris (FR)

(73) Assignees: Institut National de la Sante et de la Recherche Medicale (INSERM), Paris (FR); American University of Brirut, Beirut (LB)

( * ) Notice: Subject to any disclaimer, the term of this patent is extended or adjusted under 35 U.S.C. 154(b) by 53 days.

(21) Appl. No.: 13/515,322

(22) PCT Filed: Dec. 15, 2009

(86) PCT No.: PCT/IB2009/056035
§ 371 (c)(1),
(2), (4) Date: Sep. 20, 2012

(87) PCT Pub. No.: WO2011/073739
PCT Pub. Date: Jun. 23, 2011

(65) Prior Publication Data
US 2013/0004459 A1 Jan. 3, 2013

(51) Int. Cl.
*A61K 38/21* (2006.01)
*A61K 33/36* (2006.01)
*A01N 59/22* (2006.01)
*A61K 38/00* (2006.01)
*A61K 38/48* (2006.01)
*A61K 38/55* (2006.01)

(52) U.S. Cl.
USPC .......... 424/85.4; 424/620; 424/621; 424/623; 424/624; 514/18.9; 514/19.3; 514/20.1; 514/4.1

(58) Field of Classification Search
None
See application file for complete search history.

(56) References Cited

U.S. PATENT DOCUMENTS 7,217,413 B1   5/2007   Koken et al.

OTHER PUBLICATIONS

White et al., (2001), Leukemia and Lymphoma, vol. 40, No. 3-4, pp. 287-294.*
Kchour et al.; "Phase 2 study of the efficacy and safety of the combination of arsenic trioxide, interferon alpha, and zidovudine in newly diagnosed chronic adult T-cell leukemia/lymphoma (ATL)"; Blood, American Society of Hematology, vol. 113, No. 26, Jun. 25, 2009, pp. 6528-6532.

* cited by examiner

*Primary Examiner* — Christine J Saoud
*Assistant Examiner* — Jegatheesan Seharaseyon
(74) *Attorney, Agent, or Firm* — Whitham Curtis Christofferson & Cook, PC

(57) ABSTRACT

The present invention relates to methods, pharmaceutical compositions and kits for use in the treatment of Adult T-cell leukemia/lymphoma. More particularly, the present invention relates to a combination of an interferon, an arsenic compound and a reverse transcriptase inhibitor for the treatment of Adult T-cell leukemia/lymphoma.

6 Claims, No Drawings

```
                     SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1 cggatacccca gtctacgtgt                                         20

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
gagccgataa cgcgtccatc g                                        21

<210> SEQ ID NO 3
<211> LENGTH: 24
<212> TYPE: DNA
<213> ORGANISM: Artificial
<220> FEATURE:
<223> OTHER INFORMATION: primer

<400> SEQUENCE: 3
ccctactggc cacctgtcca gagc                                     24

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
tcagatcacc tgggacccca tc                                       22
```

METHODS, PHARMACEUTICAL COMPOSITIONS AND KITS FOR USE IN THE TREATMENT OF ADULT T-CELL LEUKEMIA/LYMPHOMA

FIELD OF THE INVENTION

The present invention relates to methods, pharmaceutical compositions and kits for use in the treatment of Adult T-cell leukemia/lymphoma.

BACKGROUND OF THE INVENTION

Adult T-cell leukemia/lymphoma (ATL) is an aggressive proliferation of mature activated CD4+ T cells associated with the human T-cell lymphotropic virus type I (HTLV-I). Leukemia develops after a very long latency period and is preceded by oligoclonal expansions of HTLV-I-infected activated T cells. These clonal expansions result from the expression of the viral transactivator protein Tax, which activates various cellular genes and creates an autocrine loop involving interleukin-2, interleukin-15, and their cognate receptors. The diversity in clinical features and prognosis of ATL patients has led to its subclassification into smoldering, chronic, lymphoma, and acute subtypes. Patients with aggressive ATL (acute and lymphoma subtypes) generally have a very poor prognosis because of intrinsic chemoresistance of malignant cells, a large tumor burden with multiorgan failure, hypercalcemia, and/or frequent infectious complications due to a profound T-cell immune deficiency. Patients with indolent ATL (ie, the chronic or smoldering subtypes) have a better prognosis. However, data from Japan showed poor long-term survival results when these patients are managed with a watchful-waiting policy until disease progression or with chemotherapy. Indeed, 4-year survival in chronic ATL is less than 30%.

It was shown that high response rates are achieved in ATL patients with the combination of the antiretroviral nucleotide analog zidovudine (AZT) and interferon alpha (IFN) (Gill P S, Harrington W Jr, Kaplan M H, et al. Treatment of adult T-cell leukemia-lymphoma with a combination of interferon alfa and zidovudine. N Engl J Med. 1995; 332:1744-1748; Hermine O, Bouscary D, Gessain A, et al. Brief report: treatment of adult T-cell leukemia-lymphoma with zidovudine and interferon alfa. N Engl J Med. 1995; 332:1749-1751; Bazarbachi A, Hermine O. Treatment with a combination of zidovudine and alpha-interferon in naive and pretreated adult T-cell leukemia/lymphoma patients. J Acquir Immune Defic Syndr Hum Retrovirol. 1996; 13(suppl 1):S186-S190; White J D, Wharfe G, Stewart D M, et al. The combination of zidovudine and interferon alpha-2B in the treatment of adult T-cell leukemia/lymphoma. Leuk Lymphoma. 2001; 40:287-294; Hermine O, Allard I, Lévy V, et al. A prospective phase II clinical trial with the use of zidovudine and interferon-alpha in the acute and lymphoma forms of adult T-cell leukemia/lymphoma. Hematol J. 2002; 3:276-282; Matutes E, Taylor G P, Cavenagh J, et al. Interferon alpha and zidovudine therapy in adult T-cell leukaemia lymphoma: response and outcome in 15 patients. Br J Haematol. 2001; 113:779-784). However, most patients eventually relapse, which underlines the need for new therapeutic approaches.

Arsenic trioxide (As) is a very effective treatment of acute promyelocytic leukemia (APL), a distinct subtype of acute myeloid leukemia that is characterized by unique clinical characteristics and a specific cytogenetic abnormality, t(15; 17), which results in a reciprocal translocation between the PML gene on chromosome 15 and the retinoic acid receptor α (RAR-α) gene on chromosome 17. Clinically, As directly targets and degrades PML/RARA fusion protein, inducing clinical remission of APL patients.

In ATL cell-lines, we have previously shown that As synergizes with IFN to induce cell cycle arrest and apoptosis (Bazarbachi A, El-Sabban M E, Nasr R, et al. Arsenic trioxide and interferon-alpha synergize to induce cell cycle arrest and apoptosis in human T-cell lymphotropic virus type I-transformed cells. Blood. 1999; 93:278-283). At the molecular level, the combination of As/IFN specifically induces proteosomal degradation of the HTLV-1 oncoprotein Tax and reversal of NF-κB activation (El-Sabban M E, Nasr R, Dbaibo G, et al. Arsenic-interferon-alpha-triggered apoptosis in HTLV-I transformed cells is associated with tax down-regulation and reversal of NF-kappa B activation. Blood. 2000; 96:2849-2855; Nasr R, Rosenwald A, El-Sabban M E, et al. Arsenic/interferon specifically reverses 2 distinct gene networks critical for the survival of HTLV-1-infected leukemic cells. Blood. 2003; 101:4576-4582). Such specific targeting of the viral oncoprotein by IFN/As treatment, reminiscent of As targeting of PML/RAR in APL, provides strong rational for combined IFN/As therapy in ATL patients. In that sense, it was previously reported the results of a phase 2 trial of As/IFN combination in 7 patients with relapsed/refractory aggressive ATL after AZT, IFN, and chemotherapy (Hermine O, Dombret H, Poupon J, et al. Phase II trial of arsenic trioxide and alpha interferon in patients with relapsed/refractory adult T-cell leukemia/lymphoma. Hematol J. 2004; 5:130-134). One patient achieved complete remission, 3 achieved partial remission, and 3 progressed. The patient in complete remission (CR) is still alive after more than 5 years of follow up. These results indicate that treatment with As and IFN is feasible and exhibits an antileukemic effect in vivo in these selected aggressive ATL patients with poor prognosis. Similarly, a transient response to As/IFN combination was reported in Japan in 2 patients with refractory acute ATL (Ishitsuka K, Suzumiya J, Aoki M, Ogata K, Hara S, Tamura K. Therapeutic potential of arsenic trioxide with or without interferon-alpha for relapsed/refractory adult T-cell leukemia/lymphoma. Haematologica. 2007; 92:719-720).

SUMMARY OF THE INVENTION

The present invention relates to a combination of an interferon, an arsenic compound and a reverse transcriptase inhibitor for use in the treatment of Adult T-cell leukemia/lymphoma.

DETAILED DESCRIPTION OF THE INVENTION

During a prospective phase 2 study, the inventors investigated the efficacy and safety of the treatment with the combination of As, IFN, and AZT in 10 newly diagnosed chronic ATL patients from the region of Mashhad in northeast Iran. They show that this combination treatment is feasible and exhibits a remarkably high response rate with moderate side effects.

Furthermore the inventors demonstrated that an arsenic trioxide/interferon-alpha association cures Tax-driven murine ATLs in vivo. Unexpectedly, this association immediately abrogates leukaemia transplantation to secondary recipients, while the primary tumour continues to grow and only exhausts much later. Treatment-triggered leukaemia initiating cell (LIC) clearance is abrogated by proteasome inhibition. The results are very reminiscent of the eradication of APL leukaemia initiating cell by therapy-induced PML/RARA degradation. They provide a rational basis for the very recent success of arsenic/interferon therapy in patients and imply that only LICs, but not the bulk of the tumour, are addicted to continued oncogene expression.

Therefore, the present invention relates to a combination of an interferon, an arsenic compound and a reverse transcriptase inhibitor for use in the treatment of Adult T-cell leukemia/lymphoma.

In its broadest meaning, the term "treating" or "treatment" refers to reversing, alleviating, inhibiting the progress of, or preventing the disorder or condition to which such term applies, or one or more symptoms of such disorder or condition.

An "interferon" or "IFN", as used herein, is intended to include any molecule defined as such in the literature, comprising for example any types of IFNs (type I and type II) and in particular, IFN-alpha, IFN-beta, INF-omega and IFN-gamma. The term interferon, as used herein, is also intended to encompass salts, functional derivatives, variants, muteins, fused proteins, analogs and active fragments thereof. The polypeptide sequences for human interferon-alpha are deposited in database under accession numbers: AAA 52716, AAA 52724, and AAA 52713. The polypeptide sequences for human interferon-beta are deposited in database under accession numbers AAC41702, NP_002167, AAH 96152, AAH 96153, AAH 96150, AAH 96151, AAH 69314, and AAH 36040. The polypeptide sequences for human interferon-gamma are deposited in database under accession numbers AAB 59534, AAM 28885, CAA 44325, AAK 95388, CAA 00226, AAP 20100, AAP 20098, AAK 53058, and NP-000610.

In a preferred embodiment the interferon is interferon-alpha. Interferon-alpha includes, but is not limited to, recombinant interferon-α2a (such as ROFERON® interferon available from Hoffman-LaRoche, Nutley, N.J.), interferon-α2b (such as Intron-A interferon available from Schering Corp., Kenilworth, N.J., USA), a consensus interferon, and a purified interferon-α product.

As used herein, the term "arsenic compound" is intended to include arsenic and any compound having the same biological properties as arsenic. The expression "compound having the same biological properties as arsenic" is understood to mean any compound which, like arsenic, is an inhibitor of phosphatase and/or is capable of creating covalent adducts by binding with dithiol groups.

In a particular embodiment, the arsenic compound is selected from the group consisting of arsenic, arsenic trioxide (As2O3), melarsoprol and arsenic sulfur derivative. Because many of the effects of arsenic are mediated through oxidative stress, agents that like arsenic promote production of reactive oxygen species are encompassed in the invention.

As used herein, the term "reverse transcriptase inhibitor" refers to any compound able to inhibit activity of the reverse transcriptase of HTVL-1. The term encompasses nucleoside analog reverse transcriptase inhibitors, nucleotide analog reverse transcriptase inhibitors and non-nucleoside reverse transcriptase inhibitors.

In a particular embodiment, the reverse transcriptase inhibitor is a nucleoside analog reverse transcriptase inhibitor selected from the group of Zidovudine (also called AZT, ZDV, and azidothymidine, and has the trade name of Retrovir), Didanosine (also called ddI, that has the trade names Videx and Videx), Zalcitabine (also called ddC and dideoxycytidine, that has the trade name Hivid), Stavudine (Stavudine, also called d4T, that has trade names Zerit and Zerit XR), Abacavir (Abacavir, also called ABC, that has the trade name Ziagen), Emtricitabine (also called FTC, that has the trade name Emtriva), and Apricitabine (also called ATC).

In a particular embodiment, the reverse transcriptase inhibitor is a nucleotide analog reverse transcriptase inhibitor selected from the group consisting of Tenofovir (also known as tenofovir disoproxil fumarate, that has the trade name Viread) and Adefovir (also known as bis-POM PMPA, that has trade names Preveon and Hepsera).

In a particular embodiment, the reverse transcriptase inhibitor is a non-nucleoside reverse transcriptase inhibitor selected from the group consisting of Efavirenz (that has the trade names Sustiva and Stocrin), Nevirapine (Viramune), Delavirdine (that has the trade name Rescriptor) and Etravirine (that has the trade name Intelence).

A further aspect of the invention relates to a method for treating Adult T-cell leukemia/lymphoma, comprising administering a subject in need thereof with amounts of an IFN, an arsenic compound and a reverse transcriptase inhibitor.

As used herein, the term "subject" denotes a mammal, such as a rodent, a feline, a canine, and a primate. Preferably, a subject according to the invention is a human.

As used herein, the term "active ingredients of the invention" is intended to refer to the inducers of Promyelocytic Leukemia protein (PML) expression, the arsenic compound and the reverse transcriptase inhibitors as defined above.

The active ingredients of the invention may be administered in the form of a pharmaceutical composition, as defined below.

Preferably, the active ingredients of the invention are administered in a therapeutically effective amount.

By a "therapeutically effective amount" is meant a sufficient amount of the actives ingredients of the invention to treat Adult T-cell leukemia/lymphoma at a reasonable benefit/risk ratio applicable to any medical treatment.

It will be understood that the total daily usage of the active ingredients of the invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific active ingredients employed; the duration of the treatment; drugs used in combination or coincidental with the specific active ingredients employed; and like factors well known in the medical arts. For example, it is well within the skill of the art to start doses of the active ingredients at levels lower than those required to achieve the desired therapeutic effect and to gradually increase the dosage until the desired effect is achieved.

The dose for administration envisaged may be for example from 1 to 50 mg per day, preferably from 10 to 15 mg per day, preferably by the intravenous route, for the arsenic compounds, from 1 to 1500 mg per kg of body weight and per day, preferably 600 to 1000 mg per kg of body weight of reverse transcriptase inhibitors, and from 1 to 20 millions of international units (M IU), per day or every two days, preferably from 3 to 9 millions of international units (M IU), per day, for the IFNs.

In a preferred embodiment, the arsenic compounds of the invention are preferably administered by the intravenous route, the reverse transcriptase inhibitors of the invention are preferably administered by the oral route, and the IFNs are administered by the intramuscular or subcutaneous route.

According to the invention, the active ingredients of the invention may be administered as a combined preparation for simultaneous, separate or sequential use in the treatment of Adult T-cell leukemia/lymphoma.

The active ingredients of the invention may be combined with pharmaceutically acceptable excipients, and optionally sustained-release matrices, such as biodegradable polymers, to form therapeutic compositions.

The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active ingredients of the invention can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The active ingredients of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In addition to the active ingredients of the invention formulated for parenteral administration, such as intravenous or intramuscular injection, other pharmaceutically acceptable forms include, e.g. tablets or other solids for oral administration; liposomal formulations; time release capsules; and any other form currently used.

The present invention relates to a pharmaceutical composition comprising an IFN, an arsenic compound and a reverse transcriptase inhibitor, and optionally pharmaceutically acceptable excipients The pharmaceutical composition as above described is particularly suitable for the treatment of Adult T-cell leukemia/lymphoma The present invention also relates to a kit containing:
a) an IFN,
b) an arsenic compound and
c) a reverse transcriptase inhibitor,
as a combined preparation for simultaneous, separate or sequential use in the treatment of Adult T-cell leukemia/lymphoma.

The present invention also relates to a combination of an IFN, and an arsenic compound for eradicating leukaemia initiating cells in a subject affected with adult T-cell leukemia/lymphoma.

As used herein, the term "leukaemia initiating cell" refers to the cells described by Dick J E. (Dick J E. Stem cell concepts renew cancer research. Blood. 2008 Dec. 15; 112 (13):4793-807) that have the unique property to allow full leukaemia development and self renew.

According to a particular embodiment, the combination as above described further comprises a reverse transcriptase inhibitor.

The invention will be further illustrated by the following figures and examples. However, these examples and figures should not be interpreted in any way as limiting the scope of the present invention.

EXAMPLE 1

Phase 2 Study of the Efficacy and Safety of the Combination of Arsenic Trioxide, Interferon Alpha, and Zidovudine in Newly Diagnosed Chronic Adult T-Cell Leukemia/Lymphoma (ATL)

The results reported below were presented in a scientific article (Kchour G, Tarhini M, Kooshyar M M, El Hajj H, Wattel E, Mahmoudi M, Hatoum H, Rahimi H, Maleki M, Rafatpanah H, Rezaee S A, Yazdi M T, Shirdel A, de Thé H, Hermine O, Farid R, Bazarbachi A. Phase 2 study of the efficacy and safety of the combination of arsenic trioxide, interferon alpha, and zidovudine in newly diagnosed chronic adult T-cell leukemia/lymphoma (ATL). Blood. 2009 Jun. 25; 113(26):6528-32. Epub 2009 May 1), which is incorporated herein by reference in its entirety.

Material & Methods

Patients' characteristics:

Ten newly diagnosed, previously untreated, chronic ATL patients were included in this prospective phase 2 study after giving informed consent. Patient enrollment started in 2007. These patients were referred to the hematology-oncology department of Ghaem and Imam Reza hospitals, Mashhad University of Medical Sciences. All ATL patients had serologic evidence of HTLV-I infection by enzyme-linked immunosorbent assay (ELISA) and confirmation of HTLV-I positivity by standard polymerase chain reaction (PCR; data not shown). Flow cytometric analysis of peripheral blood at diagnosis showed that tumor cells were CD4+, CD8−, and CD25+ (Table 1). All patients had chronic ATL according to the Shimoyama classification criteria for ATL (Shimoyama M. Diagnostic criteria and classification of clinical subtypes of adult T-cell leukaemia-lymphoma: a report from the Lymphoma Study Group (1984-87). Br J Haematol. 1991; 79:428-437). The patient's characteristics are shown in Table 1. This study was approved by the ethical committee of Mashhad University of Medical Sciences and patient informed consent was obtained in accordance with the Declaration of Helsinki

TABLE 1

Patient characteristics at initiation of treatment

| Patient no. | Age, y | Sex | LDH, xN | Lymphocyte count/μL | CD4+CD25+, % |
|---|---|---|---|---|---|
| 1 | 47 | F | 1.2 | 7000 | 41 |
| 2 | 53 | M | 1.8 | 1320 | 15 |
| 3 | 36 | M | 1.9 | 4230 | 45 |
| 4 | 53 | M | <1 | 2160 | 22 |
| 5 | 46 | F | <1 | 5100 | 42 |
| 6 | 63 | F | <1 | 5050 | 29 |
| 7 | 51 | F | <1 | 4350 | 14 |
| 8 | 77 | M | 1.7 | 7980 | 54 |
| 9 | 68 | F | 1.6 | 4990 | 40 |
| 10 | 58 | F | 1.2 | 185700 | 52 |

The last column indicates the percentage of total lymphocytes that is CD4+ and CD25+. LDH indicates lactate dehydrogenase; and ATL, adult T-cell leukemia/lymphoma. All patients had chronic ATL and did not have hypercalcemia.

Study Design and Treatment Schedule:

Treatment consisted of intravenous As (10 mg/day, 5 days/wk), subcutaneous IFN (Pooyesh Darou Pharmaceutical, Tehran, Iran; 5 million units/day), and oral AZT (900 mg/day). Arsenic was initially planned for a duration of 60 days. However, after poor tolerance in the first patient who received 60 days of As together with AZT and IFN, the protocol was amended to 30 days of As. In case of toxicity, AZT and IFN were either transiently interrupted or their dose was reduced to 600 mg/day and 3 million units per day, respectively. Arsenic dose was not reduced in case of toxicity, but As treatment was transiently interrupted. Details about treatment dose, treatment duration, and treatment interruption are listed in Table 2. Treatment of nonresponders was at the discretion of the investigator.

TABLE 2

Treatment schedule

| Patient no. | As dose, mg/d | As duration, d | As interrupt Y/N (duration) | IFN dose, MIU/d | IFN duration, d | IFN interrupt Y/N (duration) | AZT dose, mg/d | AZT duration, d | AZT interrupt Y/N (duration) |
|---|---|---|---|---|---|---|---|---|---|
| 1 | 10 | 60 | Y (15 d) | 5 | 440 | Y (15 d) | 900 | 455 | Y (15 d) |
| 2 | 10 | 30 | N | 5 | 450 | N | 900 | 30 | N |
|   |    |    |   |   |     |   | 600 | 420 | N |
| 5 | 10 | 30 | N | 5 | 90 | N | 900 | 90 | N |
|   |    |    |   | 3 | 195 | N | 600 | 180 | N |
| 6 | 10 | 30 | N | 5 | 180 | N | 900 | 180 | N |
| 7 | 10 | 30 | N | 5 | 75 | Y (15 d) | 900 | 75 | Y (15 d) |
|   |    |    |   | 3 | 165 |   | 600 | 165 | N |
| 8 | 10 | 30 | N | 5 | 75 | N | 900 | 75 | N |
| 9 | 10 | 30 | N | 5 | 90 | N | 900 | 90 | N |
|   |    |    |   | 3 | 105 | N | 600 | 160 | N |

TABLE 2-continued

Treatment schedule

| Patient no. | As dose, mg/d | As duration, d | As interrupt Y/N (duration) | IFN dose, MIU/d | IFN duration, d | IFN interrupt Y/N (duration) | AZT dose, mg/d | AZT duration, d | AZT interrupt Y/N (duration) |
|---|---|---|---|---|---|---|---|---|---|
| 10 | 10 | 30 | N | 5 | 90 | N | 900 | 90 | N |
|    |    |    |   | 3 | 105 | N | 600 | 150 | N |
| 11 | 10 | 30 | N | 5 | 90 | N | 900 | 90 | N |
|    |    |    |   | 3 | 45 | N | 600 | 60 | N |
| 13 | 10 | 30 | N | 5 | 75 | N | 900 | 75 | N |

As indicates arsenic trioxide; IFN, interferon alpha; AZT, zidovudine; Y, yes; N, no; interrupt, interruption; d, days; and MIU, million international units.

Response Criteria:

Complete remission (CR) was defined as a normalization of the complete blood count (CBC) associated with a disappearance of all measurable tumors lasting at least 1 month. Patients with persistence of less than 5% atypical lymphocytes were, however, considered in CR because this situation may be seen in healthy carriers of HTLV-I. Very good partial response (VGPR) was defined as a normalization of the CBC associated with a disappearance of all measurable tumors lasting at least 1 month, but with persistence of more than 5% atypical lymphocytes on peripheral blood smear. Partial response (PR) was defined as a decrease of more than 50% in the number of leukemia cells and in the size of all measurable tumors. No response (NR) was defined as less than 50% decrease in the number of leukemia cells or in the size of any measurable tumor, or as disease progression. Progression-free survival (PFS) was defined as the period between initiation of treatment and the date of disease progression, death, or last follow-up. Overall survival (OS) was defined as the period between initiation of treatment and the date of death or last follow-up.

Proviral Load:

The HTLV-I viral copy number per microliter of blood was calculated from the cell count and the average viral copy number per cell as assessed by quantitative PCR. Real-time quantitative PCR was performed on DNA extracted from peripheral blood mononuclear cells as previously described, using primers and Taqman probe positioned on tax gene and albumin gene for normalization. TaqMan amplification was carried out in reaction volumes of 25 μL, with the use of the qPCR MasterMix (Eurogentec, Leuven, Belgium). Each sample was analyzed in triplicate with the use of 250 ng DNA in each reaction. Thermal cycling was initiated with a 2-minute incubation at 50° C., followed by a first denaturation step of 10 minutes at 95° C. and then by 45 cycles at 95° C. for 15 seconds and 58° C. for 1 minute for tax (or 60° C. for 1 minute for albumin).

Results

Toxicity and Dose Adjustment:

Toxicity (WHO>3) occurred in 4 patients (Table 3). Most patients experienced hematologic toxicity, especially at the end of the first month of treatment (grade>1 [6 patients], grade>3 [3 patients]). Extrahematologic toxicities (grade>1 [7 patients], grade>2 [1 patient]) included gastrointestinal (nausea and vomiting) and hepatic (cytolysis and cholestasis) signs. Overall, toxicity resulted in dose reduction or transient discontinuation of treatment in 7 patients. In addition to these objective toxicities, we noted that most patients experienced severe fatigue during the last week of arsenic therapy. This was rapidly reversible after arsenic discontinuation

TABLE 3

Toxicity (WHO grade)

| Patient no. | Anemia | Neutropenia | Thrombocytopenia | Liver function | Nausea/vomiting | Other |
|---|---|---|---|---|---|---|
| 1 | 1 | 1 | 0 | 2 | 1 | 0 |
| 2 | 0 | 0 | 0 | 0 | 1 | 0 |
| 5 | 1 | 3 | 0 | 0 | 1 | Fever |
| 6 | 0 | 0 | 0 | 0 | 1 | 0 |
| 7 | 1 | 3 | 3 | 1 | 1 | 0 |
| 8 | 0 | 0 | 0 | 0 | 0 | 0 |
| 9 | 1 | 0 | 0 | 0 | 1 | 0 |
| 10 | 1 | 0 | 3* | 0 | 0 | 0 |
| 11 | 1 | 3 | 1 | 0 | 0 | 0 |
| 13 | 0 | 0 | 1 | 0 | 1 | 0 |

WHO indicates World Health Organization.
*Thrombocytopenia present before starting treatment Most patients could achieve the initially planned duration of arsenic treatment (30 days) and are still receiving maintenance therapy with AZT and IFN, albeit at reduced dose as shown in Table 2. Overall, AZT was transiently interrupted in 2 patients or given at a reduced dose in 6 patients. Similarly, IFN was transiently interrupted in 2 patients or given at a reduced dose in 5 patients. Finally, As was transiently interrupted in one patient.

Response and Survival:

All patients initially presented with symptomatic chronic ATL. The most frequent symptoms were cutaneous manifestations with maculopapular rash, severe itching, and skin ulcerations. Treatment with As, IFN, and AZT resulted in an impressive 100% response rate (Table 4). At day 30, 5 patients achieved PR and 5 patients achieved VGPR defined as a normalization of the CBC associated with a disappearance of all measurable tumors lasting at least 1 month, but with persistence of more than 5% of atypical lymphocytes on peripheral blood smear. Impressively, within 2 to 4 weeks, skin lesions almost disappeared. Interestingly, in the 7 patients for whom initial and day-30 DNA was available, HTLV-I proviral load significantly decreased from an average of 1415 copies/μL blood to 226 copies/μL (P<0.05; Table 5). All patients continued to improve their response (Table 4). Indeed, disease evaluation at last follow up showed that 7 patients were in CR, 2 patients were in VGPR (solely because of the presence of 6% and 8% of atypical lymphocytes on peripheral blood smear, respectively), and 1 patient was in PR (after a short follow up of 2 months, his lymphocytosis decreased from 185 000×109/L to 6400×109/L). After a median follow-up of 8 months (range, 2-15 months), all patients are still alive; none of them relapsed or progressed.

TABLE 4

Response and follow-up

| Patient no. | Response day 30 | PFS, mo | Status at last F/U | Survival, mo |
|---|---|---|---|---|
| 1 | VGPR | 15+ | CR | 15+ |
| 2 | PR | 15+ | CR | 15+ |
| 5 | VGPR | 12+ | VGPR* | 12+ |
| 6 | PR | 10+ | CR | 10+ |
| 7 | VGPR | 8+ | CR | 8+ |
| 8 | PR | 3+ | CR | 3+ |
| 9 | PR | 8+ | CR | 8+ |
| 10 | VGPR | 4+ | CR | 4+ |
| 11 | VGPR | 5+ | VGPR† | 5+ |
| 13 | PR | 2+ | PR‡ | 2+ |

All patients were alive at end of study;
no patient had relapse/progression.
CR indicates complete remission;
PR, partial response;
VGPR, very good partial response;
PFS, progression-free survival; and
F/U, follow-up.
*Eight percent atypical lymphocytes on peripheral blood smear.
†Six percent atypical lymphocytes on peripheral blood smear.
‡Lymphocytosis decreased from 185 000 to 6400.

TABLE 5

Variation of HTLV-I proviral load between initiation of treatment and day 30

| Patient no. | Initial viral load, copy/μL | Viral load at day 30, copy/μL | Viral load at day 30, % from initial |
|---|---|---|---|
| 1 | 1990 | 336 | 17 |
| 2 | 84 | 33 | 40 |
| 3 | 999 | 838 | 84 |
| 6 | 1081 | 63 | 6 |
| 7 | 196 | 64 | 33 |
| 8 | 3747 | 182 | 5 |
| 9 | 1805 | 65 | 4 |
| Average | 1415 | 226* | 27 |
| SD | 1256 | 290 | 29 |

The viral copy number per microliter of blood was calculated from the cell count and the average viral copy number per cell as assessed by quantitative PCR as described in "Proviral load."
SD indicates standard deviation.
*P < .05.

Discussion:

In this prospective phase 2 study, we show promising clinical results of an As/IFN/AZT combination in 10 newly diagnosed chronic ATL patients from northeast Iran. An impressive 100% response rate was observed, including 7 patients who achieved CR, 2 patients who achieved VGPR (clinical and biologic CR except for the presence of more than 5% atypical lymphocytes on peripheral blood smear), and 1 achieved PR (after a short follow-up of 2 months, lymphocytosis decreased by more than 95%). Although this impressive response rate could be partly explained by the presence of AZT and IFN in the As/IFN/AZT triple combination, it is noteworthy that the response rate and particularly the CR rate with AZT/IFN alone in published studies (Gill P S, Harrington W Jr, Kaplan M H, et al. Treatment of adult T-cell leukemia-lymphoma with a combination of interferon alfa and zidovudine. N Engl J Med. 1995; 332:1744-1748; Hermine O, Bouscary D, Gessain A, et al. Brief report: treatment of adult T-cell leukemia-lymphoma with zidovudine and interferon alfa. N Engl J Med. 1995; 332:1749-1751; Bazarbachi A, Hermine O. Treatment with a combination of zidovudine and alpha-interferon in naive and pretreated adult T-cell leukemia/lymphoma patients. J Acquir Immune Defic Syndr Hum Retrovirol. 1996; 13(suppl 1):S186-S190; White J D, Wharfe G, Stewart D M, et al. The combination of zidovudine and interferon alpha-2B in the treatment of adult T-cell leukemia/lymphoma. Leuk Lymphoma. 2001; 40:287-294; Hermine O, Allard I, Lévy V, et al. A prospective phase II clinical trial with the use of zidovudine and interferon-alpha in the acute and lymphoma forms of adult T-cell leukemia/lymphoma. Hematol J. 2002; 3:276-282; Matutes E, Taylor G P, Cavenagh J, et al. Interferon alpha and zidovudine therapy in adult T-cell leukaemia lymphoma: response and outcome in 15 patients. Br J Haematol. 2001; 113:779-784) is less than what is observed in this study. Moreover, the highest rates of response were previously reported with the use of high doses of AZT and high doses of IFN (6 million units/m2), whereas most of our patients received a much lower dose of IFN (total dose of 5 to 3 million units). Finally, although the follow-up of our study is relatively short (median follow-up of 8 months), none of the patients relapsed or progressed. Altogether, these results strongly suggest that As significantly improved the response rate of AZT/IFN.

The triple combination of As/IFN/AZT was feasible with moderate and manageable side effects. Hematologic toxicity necessitated transient treatment interruption or dose reduction in some patients. Extrahematologic toxicity consisted mainly of gastrointestinal discomfort. However, it is noteworthy that severe fatigue was noted during the last week of arsenic therapy in most patients. This was rapidly reversible after arsenic discontinuation. Hence, a shorter duration of arsenic (3 weeks) may be associated with increased tolerance and should be explored in future trials. Overall, based on this study, in patients with chronic ATL, the recommended starting dose of the 3 agents during the first month of treatment would be AZT (900 mg/day), IFN (5 million IU/day), and As (10 mg/day). Dose reduction of AZT (to 600 mg/day) and IFN (to 3 million IU/day) should be done in case of severe toxicity. This should be followed by maintenance AZT/IFN at the same dose. However, a phase 1 study is now recommended to establish the maximal tolerated dose for each drug in this highly effective combination regimen.

As for the mechanism of action, we have previously shown that, ex vivo, the combination of As and IFN selectively kills HTLV-I-infected cells, through reversion of the constitutive activation of NF-κB and degradation of the Tax oncoprotein by the proteasome. Proteasome-mediated degradation of Tax by As/IFN is reminiscent of the proteasome-mediated degradation of PML-RAR by As in APL. After many years of controversy, it is now established that the viral transactivator Tax plays a critical role in initiating the leukemic process, because Tax mice transgenics develop a disease with striking ATL features. We recently demonstrated that As and IFN cooperate to cure mouse ATL derived from these Tax transgenics. Surprisingly, this combination does not trigger an immediate growth arrest or apoptosis but rather selectively eradicates leukemia-initiating cells (LICs). This strongly suggests that LICs, rather than the bulk of the leukemia, are addicted to continuous oncogene expression. Hence, addition of As to AZT/IFN, through elimination of LICs, may result in long-term disease eradication and eventual cure. The short follow-up of our study does not allow conclusive evidence regarding overall survival. Long-term follow-up of patients treated by the combination of As/IFN/AZT will demonstrate whether this high rate of complete remission will translate in terms of disease eradication and patients cure.

In aggressive ATL, preliminary results from 2 acute ATL patients suggest that addition of As to AZT/IFN during the induction phase may result in severe tumor lysis syndrome. Hence, an attractive strategy in that setting would be induction therapy with AZT/IFN to decrease the tumor bulk followed by addition of arsenic at low tumor burden to achieve CR, in a clinical situation similar to chronic ATL patients.

In conclusion, treatment of ATL with As, IFN, and AZT is feasible and exhibits an impressive response rate with moderate toxicity in patients with chronic ATL. Although the follow-up was relatively short (8 months), none of the patients have relapsed, raising hopes that extinction of viral replication (AZT) and Tax degradation (As/IFN) may eradicate the disease. These clinical results strengthen the concept of oncogene-targeted cancer therapy.

EXAMPLE 2

Therapy-Induced Selective Loss of Leukaemia-Initiating Cells in Murine ATL

Experimental Procedures:
Mice:
We used the ATL mouse model of Hasegawa (Hasegawa et al., 2006). To test the effect of different targeted therapies, we established a rapid and reproducible model of disease by direct intra-peritoneal transfer of $10^6$ spleen cells from Tax transgenic mice into SCID mice (Charles River, USA). Expression of Tax was only detectable at very low levels by Q-PCR. All murine protocols were approved by the Institutional Animal Care and Utilization Committee (IACUC) of the American University of Beirut. All animals were housed in specific pathogen-free housing. Animals were sacrificed by cervical dislocation following deep anesthesia with isoflurane.

Treatments:
Arsenic trioxide was obtained from Sigma-Aldrich (St Louis, Mo., USA) and recombinant human interferon-alpha (IFN) (Roferon®) from Hoffman-La Roche (Basel, Switzerland). The proteasome inhibitor PS341 or bortezomib (Velcade®) was purchased from Millenium Pharmaceuticals. For in vivo experiments, mice received arsenic (5 µg/g/day) intra-peritoneally, IFN ($10^6$ IU/day) subcutaneously, bortezomib (0.5 mg/Kg/day) through mini-osmotic pumps (Alzet, Charles river). These doses are comparable to those previously in other mouse models and predicted to yield plasma concentrations similar to those found in patients (Nasr et al., 2008). None of the different individual or combination treatment regimen was toxic in normal SCID mice (100% survival for more than 3 months; n=3 for each condition). In ex-vivo experiments, malignant cells from Tax-transgenic mice were treated in vitro with either arsenic (1 µM), IFN (1000 IU) or a combination of arsenic/IFN for up to 48 h.

Histopathological and Laboratory Examination:
Tissues from both treated and untreated mice were fixed in neutral buffer formalin (Sigma), then embedded in paraffin, sectioned, stained with hematoxylin and eosin (H&E), and examined by light microscopy. Ki-67 expression was assessed by immuno-histochemistry using rat anti-mouse monoclonal antibody Ki-67, clone TEC-3. Peripheral blood smears were prepared using Giemsa staining White blood cell (WBC) counts, serum calcium and serum lactate dehydrogenase levels were determined using routine clinical laboratory techniques.

The terminal deoxynucleotidyl transferase-mediated nick end labeling (TUNEL) assay was performed on deparaffinized 5-µm sections, treated with proteinase K (20 µg mL$^{-1}$) for 15 minutes at room temperature. The number of TUNEL-positive cells was assessed in three different microscopic fields for each organ studied (liver, lung and spleen), by two pathologists, on an Olympus ProvisAX70 microscope (Olympus Optical), with wide-field eye-piece number 26.5. At 600× magnification, this wide-field eyepiece provided a field size of 0.244 mm$^2$. Mitoses were counted with the same methods, and the results were expressed as the mean number of apoptotic cells or of mitoses per field at 600× magnification.

Cell Cycle Analysis and TUNEL Assay on Isolated Splenocytes:
Splenocytes were harvested, filtered, washed twice with cold PBS, fixed in 100% ethanol at −20° C. and kept overnight at −20° C. Subsequently, cells were rinsed with PBS, treated with Tris-HCl buffer (pH 7.4) containing 1% DNase free-RNase A and stained with propidium iodide (PI) (60 mg/ml final). The distribution of cell cycle phases with different DNA contents was determined using a FACScan flow cytometer (Becton Dickinson). In each sample, 10000 ungated events were acquired. Analysis of cell cycle distribution (including apoptosis) was performed using the CellQuest software (Becton Dickinson).

The TUNEL assay was also used to monitor splenocyte apoptosis. The assay was performed according to the manufacturer's (Roche) recommendations. Fluorescein-conjugated dUTP incorporated in nucleotide polymers was detected and quantified using flow cytometry. Approximately 10000 cells per sample were acquired and analyzed using the CellQuest software (Becton Dickinson).

Quantitative PCR:
Spleens were harvested and real time PCR or RT-PCR using a LightCycler (Roche Diagnostics) was used to quantitate the absolute Tax DNA content, or the absolute Tax mRNA expression, using a LightCycler FastStart DNA Master kit, or Light Cycler RNA Master kit respectively. We also used the Lightcycler 4.05 software version. The Tax primers SK43I (5'-CGGATACCCAGTCTACGTGT-3') and SK44I (5'-GAGCCGATAACGCGTCCATCG-3'), and probes SK4I-FL (5'-CCCTACTGGCCACCTGTCCAGAGC-FL-3') and SK4I-LC (5'-LC Red640-TCAGA TCACCTGGGAC-CCCATCPH-3') were designed in collaboration with Tib-MolBiol. We also used circulating ATL leukaemia cells from two patients with acute ATL after informed consent. For Electrophoretic Mobility Shift Assay (EMSA), nuclear extracts from splenocytes of treated and untreated mice were prepared as described (El-Sabban et al., 2000).

Statistical Analysis:
Survival curves were calculated according to the method of Kaplan and Meier. Overall survival is defined as the time from injection of ATL cells to death from any cause. Mice that were still alive were censored at the time they were last known to be alive. The analyses were performed using SPSS software version 15.0 (SPSS). The p value was obtained by log-rank statistical analysis.

Results & Discussion:
To explore the in vivo efficacy of IFMα/As$_2$O$_3$, we established an ATL transplantation model in which $10^6$ ATL spleen cells from Tax transgenic mice were inoculated into SCID mice. In the same manner as in the original transgenic mice, recipients developed a massive hyperleukocytosis, splenomegaly, hypercalcemia and multiple organ invasion, and died within 28 days. We first questioned whether these mouse ATL cells would respond ex vivo to the IFMα/As$_2$O$_3$ combination. IFNα or arsenic triggered apoptosis in less than 20% Tax transgenic cells. Their combination killed over 80% of cells after an ex vivo overnight exposure, while normal murine lymphocytes were unaffected. Tax degradation by the proteasome could not be demonstrated in these ATL cells, because the protein was undetectable by Western blot analysis, exactly as in primary human ATLs. Tax mRNA levels were, however, very similar in primary mouse and human ATL cells, but 1000-fold higher in the HuT-102 cell-line, where Tax protein was easily detectable.

To investigate any survival benefit, mice were treated from days 6 to 30 with IFNα, $As_2O_3$ or both, using doses validated in other mice models. A significant survival advantage was seen in animals receiving IFNα or $As_2O_3$ alone, but animals receiving the IFNα/$As_2O_3$ combination were often cured, particularly when a second course of therapy was administered. IFNα/$As_2O_3$ treatment had to be continuous, because protocols in which mice were treated for five days a week never yielded any cure. Such exquisite ex vivo and in vivo sensitivity to IFMα/$As_2O_3$ of both human HTLV-I-infected ATL cells and mouse Tax-driven ATLs strongly supports Tax degradation as an essential contributor in the response to this combination.

To dissect the molecular basis for this curative action, we examined cell proliferation and apoptosis in established murine ATLs treated for 3 days with the association. Complete reversal of NFκB activation was observed in spleen ATL cells, and calcium plasma levels returned to normal. Unexpectedly, while this 3-day treatment decreased the number of circulating ATL cells, it did not affect spleen weight. With 6 days of treatment, only IFNα led to significant spleen weight reduction, while $As_2O_3$ or IFNα/$As_2O_3$ paradoxically increased it. Thus, in contrast to ex vivo treatment, primary mouse ATLs did not undergo massive cell growth arrest or apoptosis in vivo. Interestingly, a dramatic increase in WBC counts was observed when mice received a proteasome inhibitor (PS341) together with IFNα/$As_2O_3$, which is consistent with the idea that proteasome-mediated Tax degradation contributes to the response to therapy.

We then administered the IFNα/$As_2O_3$ combination for 15, 20 and 24 days, starting on day 6 post-inoculation. At all time-points, this treatment moderately affected spleen weight, but resulted in diminished circulating ATL cells and reduced micro-metastases within sinusoids of the liver parenchyma. Yet, pathological examination demonstrated persistent and massive tissue invasion and high expression of the proliferation marker Ki67. Indeed, although the frequency of mitoses in leukaemic infiltrates of the spleen and liver decreased 2-fold, no significant cell-cycle arrest was observed in ATL spleenic cells, even after two weeks of treatment. Because NFκB shut-off would be expected to sensitize cells to apoptosis, we analyzed spleens and livers for TUNEL-positive infiltrating tumor cells. Modest increases in in vivo labeling were noted at days 21 and 26 and ex vivo TUNEL labeling of spleen ATL cells increased at day 26 only. Analysis of primary recipients sacrificed at day 30 demonstrated significant tumor regressions, but never clearance. Yet, at day 180, the cured animals were indistinguishable from non-inoculated controls. Thus, IFNα/$As_2O_3$ induces only delayed apoptosis, which is most likely responsible for the ultimate ATL eradication.

Such paradoxical uncoupling between ongoing ATL cell growth under therapy, late apoptosis, and finally complete disappearance of ATL cells in an immunodeficient animal clearly sets this combination aside from classical anti-cancer regimens. We thus questioned whether the IFNα/$As_2O_3$ combination could selectively affect ATL LICs, secondarily yielding progressive leukemia exhaustion. After 3 days of treatment with IFNα/$As_2O_3$, similar amounts of spleen leukaemia cells were injected into secondary recipients. The inoculated cells did not display any evidence or cell-cycle arrest or TUNEL labeling Yet, a dramatic increased survival of secondary recipients was observed with inoculates originating from 3-days treated mice rather than from untreated ones, suggesting that IFNα/$As_2O_3$ specifically targets ATL LICs. Using serial dilutions of ATL cells from untreated versus IFNα/arsenic-treated mice, a sharp difference in the survival time of secondary transplant recipients was observed, formally demonstrating that IFNα/$As_2O_3$ dramatically decreases LIC abundance in the leukaemia cell inoculate. Interestingly, a delayed apoptosis was noted in ATL cells collected from untreated secondary transplants inoculated with blasts from IFNα/$As_2O_3$-treated primary recipients. Furthermore, no ATL developed in tertiary recipients of ATL cells from these mice. Thus, the 3-day IFNα/$As_2O_3$ exposure in primary mice triggers delayed ATL cell apoptosis and later disease exhaustion in otherwise untreated secondary and tertiary transplants. In sharp contrast, when proteasome activity was inhibited during the course of IFNα/$As_2O_3$ therapy in primary recipients, the drop in LIC content was much less pronounced in secondary recipients and all tertiary mice died of ATL.

These results strongly suggest that the in vivo efficacy of the IFNα/$As_2O_3$ combination in ATL reflects the rapid loss of LIC, most likely through the proteolysis of Tax, unraveling the mechanisms behind the success of $As_2O_3$/IFNα/zidovuline therapy in human ATL. LICs, even when they are abundant as do not necessarily die, but they irreversibly loose self-renewal, and inevitably disappear in primary mice or in secondary transplant recipients. Our observations are fully consistent with the fact that one of the first actions of leukaemia oncogenes is to confer to progenitor cells the ability to expand or self-renew. The molecular pathways involved in Tax degradation are not yet elucidated, but may share some similarities with those involved in PML degradation, since Tax is both ubiquitinated and sumoylated. In addition to Tax loss, PML degradation by $As_2O_3$ may contribute to LIC cell-cycle entry and exhaustion, explaining the paradoxical initial increase in tumor mass. However, although $As_2O_3$ reduced LIC abundance it never cleared the disease.

ATL is currently an incurable disease. Our approach to its treatment has relied on the idea that HTLV-I is the direct initiator of ATL. Yet, while the antiviral zibovuline/IFNα combination induces 35-50% complete response (CR) rates and significantly prolongs survival as compared with DNA-damaging agents, most patients eventually relapse and die. Moreover, this regimen does not eradicate LICs because discontinuation of therapy rapidly results in disease recurrence. The efficacy of the IFNα/$As_2O_3$ regimen was previously assessed in multi-relapsed IFNα-resistant patients and, nevertheless, it showed some success. Our latest trial in de novo patients with the $As_2O_3$/IFNα/zidovudine combination has yielded unprecedented results (90% CR, no relapse to date). How do the present mouse data contribute to our understanding of these provocative clinical results? First, they imply that the IFNα/$As_2O_3$ association most likely acts through Tax degradation, identifying it as a HTLV-I targeted therapy. Note that the regimen used in mice did not comprise zidovudine, because here Tax is under the control of the Lck promoter, rather than being expressed by a replication-competent retrovirus. Moreover, the zidovudine/IFNα combination was not better that IFNα alone. The scheduling issues (7 days a week much better than 5 days a week) may also lead to adjustment in the current 5 days a week patient regimen. Second, our studies establish that the selective clearance of LICs is triggered by oncogene degradation, implying that theses cells are exquisitely addicted to continuous oncogene expression or function). To our knowledge, these results are the first to decipher the uncoupling between massive LIC loss and continued proliferation of the tumor bulk. In this respect, the kinetics of disease clearance in the $As_2O_3$/IFNα/zidovudine-treated patients were significantly slower than tumor debulking with cytotoxic drugs. When only partial responses with $As_2O_3$/IFNα/zidovudine were observed on day 30, complete remissions unfurled over the next months, fully in line with the mice model. Our mice results would predict that patients responding to $As_2O_3$/IFNα/zidovudine are unlikely to relapse, raising the prospect of a possible cure for ATL. Collectively, our findings have broad implications for the elaboration of novel cancer therapies based on oncogene degradation, as well as for the definition of the relevant end-points in clinical trials with such drugs.

REFERENCES

Throughout this application, various references describe the state of the art to which this invention pertains. The disclosures of these references are hereby incorporated by reference into the present disclosure.

The invention claimed is:

1. A method for treating Adult T-cell leukemia/lymphoma in a patient in need thereof, comprising
administering to said subject a dose from 1 to 20 million international units (MIU) per day of an interferon-alpha, a dose from 1 to 50 mg per day of arsenic trioxide and a dose from 1 to 1500 mg per kg of body weight per day of zidovudine.

2. The method according to claim 1 wherein said arsenic trioxide is administered at a dose from 10 to 15 mg per day.

3. The method according to claim 1 wherein said zidovudine is administered at a dose from 600 to 1000 mg per kg of body weight per day.

4. The method according to claim 1 wherein said interferon-alpha is administered at a dose from 3 to 9 MIU per day.

5. The method according to claim 1 wherein said arsenic trioxide is administered by an intravenous route, said zidovudine is administered by an oral route, and said interferon-alpha is administered by an intramuscular or subcutaneous route.

6. The method according to claim 1 wherein said interferon-alpha, said arsenic trioxide and said zidovudine are administered as a combined preparation for simultaneous, separate or sequential use.

* * * * *

UNITED STATES PATENT AND TRADEMARK OFFICE
CERTIFICATE OF CORRECTION

PATENT NO. : 8,784,797 B2  
APPLICATION NO. : 13/515322  
DATED : July 22, 2014  
INVENTOR(S) : De The et al.

Page 1 of 1

It is certified that error appears in the above-identified patent and that said Letters Patent is hereby corrected as shown below:

Title Page: Item (73), Assignees: please correct the second-named assignee as follows:
Please delete "Brirut" and insert -- Beirut -- so it reads American University of Beirut Signed and Sealed this
Sixth Day of January, 2015

Michelle K. Lee
*Deputy Director of the United States Patent and Trademark Office*